(12) United States Patent
Strauss et al.

(10) Patent No.: US 12,410,423 B2
(45) Date of Patent: Sep. 9, 2025

(54) SILICA ENCAPSULATED DNA ON MAGNETIC NANOPARTICLES

(71) Applicant: MICROSOFT TECHNOLOGY LICENSING, LLC, Redmond, WA (US)

(72) Inventors: Karin Strauss, Seattle, WA (US); Weida Chen, Zürich (CH); Robert Grass, Zürich (CH); Alexander Xavier Christof Kohll, Zürich (CH); Bichlien Hoang Nguyen, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 17/341,206

(22) Filed: Jun. 7, 2021

(65) Prior Publication Data
US 2021/0291134 A1 Sep. 23, 2021

Related U.S. Application Data (62) Division of application No. 16/017,682, filed on Jun. 25, 2018, now Pat. No. 11,059,016.

(51) Int. Cl.
*B01J 13/22* (2006.01)
*B22F 1/054* (2022.01)
(Continued)

(52) U.S. Cl.
CPC .......... *C12N 15/1013* (2013.01); *B01J 13/22* (2013.01); *B22F 1/054* (2022.01); *B22F 1/102* (2022.01);
(Continued)

(58) Field of Classification Search
CPC .......... B22F 1/054; B22F 1/102; C07H 21/04
See application file for complete search history.

(56) References Cited

U.S. PATENT DOCUMENTS

2008/0261045 A1* 10/2008 Glass .............. A61K 9/1676
427/213.3
2010/0092384 A1* 4/2010 Bumb ............. G01N 33/54346
424/9.4

FOREIGN PATENT DOCUMENTS

CN 107112105 A 8/2017
WO WO-2015192149 A2 * 12/2015 ............. A61K 38/05

OTHER PUBLICATIONS

Puddu et al. vol. 8, No. 3, pp. 2677-2685. ACSNANO, 2014 (Year: 2014).*

(Continued)

*Primary Examiner* — Evelyn Y Pyla
(74) *Attorney, Agent, or Firm* — Benjamin Keim; Newport IP, LLC (57) ABSTRACT

A data storage medium is disclosed comprising a substrate covered with alternating layers of a polycationic molecule and artificially synthesized DNA molecules encoding digital information. The magnetic substrate may be a metallic nanoparticle formed from a metal such as iron or cobalt. The polycationic molecule may be polyethyleneimine (PEI). The DNA is protected from degradation by encapsulation in silica. A process for stably storing DNA is also disclosed. Stored DNA may be freed from the silica for sequencing or other analysis by washing the silica-coated DNA with a buffered hydrogen fluoride solution. Storage densities of more than 7% DNA by weight are achieved on nanoparticles.

16 Claims, 6 Drawing Sheets

(51) Int. Cl.
  *B22F 1/102* (2022.01)
  *B22F 1/16* (2022.01)
  *C07H 21/04* (2006.01)
  *C12N 15/10* (2006.01)
  *G16B 30/00* (2019.01)
  *B82Y 10/00* (2011.01)

(52) U.S. Cl.
  CPC ............... *B22F 1/16* (2022.01); *C07H 21/04* (2013.01); *G16B 30/00* (2019.02); *B82Y 10/00* (2013.01)

(56) References Cited

OTHER PUBLICATIONS

"Office Action Issued in European Patent Application No. 19748985.9", Mailed Date: Feb. 1, 2022, 7 Pages.
"Office Action Issued in Indian Patent Application No. 202047052404", Mailed Date: Oct. 28, 2022, 5 Pages.
Office Action Received for Chinese Application No. 201980041050.5, mailed on Dec. 25, 2023, 11 pages (English Translation Provided).
"Notice of Allowance Issued in European Patent Application No. 19748985.9", Mailed Date: Sep. 1, 2023, 8 Pages.
Decision to grant a European patent pursuant to Article 97(1) Received for European Application No. 19748985.9, mailed on Jan. 5, 2024, 02 pages.
Office Action Received for Chinese Application No. 201980041050.5, mailed on May 24, 2024, 8 pages (English Translation Provided).

\* cited by examiner

SILICA ENCAPSULATED DNA ON MAGNETIC NANOPARTICLES

CROSS-REFERENCE TO RELATED APPLICATION

This application is a divisional of, and claims priority to, U.S. patent application Ser. No. 16/017,682, filed Jun. 25, 2018, and entitled "Silica Encapsulated DNA on Magnetic Nanoparticles," the entire contents of which are incorporated herein by reference.

BACKGROUND

The volume of digital information is increasing at an exponential rate. This vast increase in the amount of digital information may outpace the ability of conventional storage technologies. One promising technology for storing large amounts of digital information is deoxyribonucleic acid (DNA). DNA is well known as a molecule that can store genetic information. However, DNA can also function as a storage medium for digital information. Multiple different groups have successfully converted computer files into a string of nucleotide bases, created synthetic DNA encoding that string, sequenced the synthetic DNA, and then recovered the original digital information with 100% accuracy.

As a storage medium, DNA has potential advantages over conventional optical and magnetic media in terms of information densities and stability. Storage using DNA can achieve data density of over 200 petabytes (i.e., 200 million gigabytes) per gram which is much higher than possible with conventional media. With DNA it is possible that all the digital information in the world could be stored in a single room. DNA can also provide better long-term storage. Magnetic and optical media can wear out within 5 to 10 years. However, readable DNA has been recovered from fossils hundreds of thousands of years old.

Longevity of DNA, however, depends on storage conditions. DNA is susceptible to degradation by heat, enzymes, mutagenic chemicals, and ionizing radiation. When stored in solution DNA is stable for approximately 10 years, which is the same timescale as other storage media. Storage techniques that provide long-term stability and high data density improve the usability of DNA as a storage medium for digital information.

SUMMARY

This disclosure provides structures and methods for stably storing DNA through encapsulation in silica. The DNA is adsorbed to a substrate which provides a structure that may be encased in silica together with the DNA. The substrate may have any shape including but not limited to a sphere or a flat surface. In an implementation the substrate is a nanoparticle. Encasing DNA in silica may involve multiple steps and the physical processing may be aided by the use of magnetism to separate DNA from a solution or supernatant. Thus, the substrate may be magnetized. The substrate may have a strong saturation magnetization such as, for example, greater than 50 electromagnetic units (EMU) per gram. Metals may have a strong saturation magnetization. In an implementation, the substrate may be a metal such as iron (Fe), cobalt (Co), or nickel (Ni). A surface layer of the substrate may be functionalized such as by the addition of carbon and/or charged organic groups. In an implementation, functionalization of the substrate may impart a negative charge to its surface creating a negatively-charged magnetic substrate.

Silica encapsulation may be performed by exposing the DNA to a tetra alkoxysilane such as tetraethyl orthosilicate (TEOS). Exposing the DNA to the silica-containing compound may occur over a prolonged period of time such as multiple hours or days. Encapsulation in silica protects the DNA from DNA degrading agents such as reactive oxygen species (ROS). Encapsulation in silica may hermetically seal the DNA under glass thereby protecting it from chemical attack, high temperatures, and humidity. This increases the durability of DNA and makes it a viable media for long-term storage of digital information.

DNA density is increased by creating multiple layers of DNA on the substrate. DNA is a negatively-charged molecule and may be layered together with a polycationic molecule such as a polycationic polymer. As used herein, "polycationic molecule" means a molecule that has three or more separate sites which could potentially be positively charged. In an implementation, the polycationic molecule is polyethyleneimine (PEI). Multiple alternating layers of DNA and the polycationic molecule may be adsorbed to the surface of the substrate. Multiple layers of DNA increase the amount of DNA that can be stored per unit of volume or weight as compared to a substrate having only a single layer of DNA. In an implementation using nanoparticles coated with four layers of DNA, the density may exceed 7% DNA by weight. Multiple layers of DNA on a flat surface (e.g. a 2D structure) may achieve loading of about 400-500 ng/cm$^2$.

Following storage, the DNA may be released from the silica encapsulation by contact with an etching solution that dissolves silica without harming DNA. In an implementation, the etching solution is a buffered hydrogen fluoride solution. Once released from encapsulation, the pH is adjusted to neutral (e.g., 6-8) and polyanionic molecules are added to displace the DNA from the polycationic molecules. The DNA may then be sequenced or otherwise processed. The sequence of nucleotide bases in the DNA may be decoded to obtain stored digital information.

These structures and techniques described in this disclosure have applications for storing synthetic DNA encoding digital information but are equally suitable for storing naturally occurring DNA.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method (s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Polynucleotides such as DNA and ribonucleic acid (RNA), including polynucleotides that have unnatural bases, may be used to store digital information by designing a sequence of nucleotide bases that encodes the zeros and ones of the digital information. There are various techniques and encoding schemes known to those of skill in the art for using nucleotide bases to represent digital information. Advantages of using DNA rather than another storage media for storing digital information include information density and longevity. The DNA storage structure and methods described in this disclosure can improve both information density and longevity relative to other techniques for storing DNA. The contents of the disclosure may be used with any type of polynucleotide, thus references to "DNA" are illustrative and not intended to limit the application to only DNA.

In an implementation, metallic nanoparticles may be used as a core onto which DNA is layered and then the entire particle is encapsulated in silica. One type of suitable nanoparticle is "TurboBeads" available from TurboBeads LLC (Zurich, Switzerland). TurboBeads are described in Grass et al., *Covalently Functionalized Cobalt Nanoparticles as a Platform for Magnetic Separations in Organic Synthesis*, 46 Angew. Chem. Int. Ed. 4909 (2007). As used herein, "nanoparticles" are particles having a diameter of approximately 100 nm or less. Some nanoparticles such as TurboBeads may have a diameter of approximately 50 nm. "Metallic" or "metal" as used herein refers to any element or alloy of elements commonly classified as a metal in the periodic table. However, metal oxides are not included in the definition of "metallic" or "metal." The techniques of this disclosure may be implemented using particles other than TurboBeads including particles having a diameter greater than 100 nm.

Substrates other than nanoparticles may also be used for storing DNA. For example, larger particles, the inside walls of a vessel, a flat surface, (e.g., a sheet of material, flexible tape, glass, plastic, etc. may be coated with alternating layers of DNA and a polycationic molecule to create a multilayered structure for stably storing DNA. The substrate, be it a particle or another shape, may be magnetic or nonmagnetic.

Magnetic properties of nanoparticles may aid in the separation of nanoparticles from supernatants or other solutions used during the process of layering DNA onto the surface of the nanoparticle and/or encapsulating the nanoparticle in silica. Physical separation of very small particles from a solution may be tedious and technically challenging. Magnetic separation permits collection of the nanoparticles and removal of supernatant or other solution without drying. Additionally, bigger volumes can easily be used, increasing the amount of collectable encapsulates and recoverable DNA as compared to drying. The term "separating" refers to a partial or complete separation of nanoparticles and solution. In case of an incomplete/insufficient separation, one or more additional separation steps may be added.

One magnetic property is "saturation magnetization." The saturation magnetization of a ferromagnetic material is a quantity that represents the magnetization that results when all the magnetic dipoles in a solid piece are mutually aligned with the external magnetic field. Saturation magnetization is the value of the magnetization of the ferromagnetic body when the easy magnetization axis of the body and the external magnetic field direction match. The saturation magnetization is equal to the product of the net magnetic moment for each atom and the number of atoms present. The term magnetic moment normally refers to a system's magnetic dipole moment the component of the magnetic moment that can be represented by an equivalent magnetic dipole: a magnetic north and south pole separated by a very small distance. The magnetic dipole moment of an object is readily defined in terms of the torque that object experiences in a given magnetic field.

Saturation magnetization may be measured by electromagnetic units (EMU) in which current is defined via the force existing between two thin, parallel, infinitely long wires carrying it, and charge is then defined as current multiplied by time. A larger saturation magnetization may increase separation speed relative to a smaller saturation magnetization, but smaller saturation magnetizations will only slow not stop separation. In an implementation, a saturation magnetization of the nanoparticles may be greater than 50 EMU per gram.

The substrate such as the nanoparticles may also exhibit "soft" magnetic behavior and have zero or near-zero magnetic hysteresis. Soft magnetic materials are those materials that are easily magnetized and demagnetized. Magnetic hysteresis is the delay in change of the magnetization of a ferromagnet when an external magnetic field is applied. Materials with low or zero hysteresis change rapidly in response to an external magnetic field.

A metallic core may be functionalized to enable adsorption of DNA to its surface. Adsorption is the adhesion of atoms, ions or molecules from a gas, liquid or dissolved solid to a surface. This process creates a film of the adsorbate on the surface of the adsorbent. "Functionalization" as used herein means introduction of functional groups to a surface. For example, TurboBeads are carbon-coated nanoparticles functionalized with chloro, nitro, amino, sulfonate, or other functional groups. The functional groups may be selected in part based on their charge. Thus, the nanoparticle may be coated with function groups that in part a negative charge to its surface. The negative charge provides a surface to which a positively charged molecules such as a polycationic polymer are electrostatically attracted. The positively charged molecules in turn provide a surface to which negatively-charged DNA may adsorb. Repeated contacting of the positively charged molecules in the DNA to the nanoparticle can add successive layers surrounding the metallic core. The term "contacting" refers to any suitable way of contacting one substance with another as described herein in the context of building layers on nanoparticles. Thus, "contacting" includes a simple addition as well as intense mixing.

The term "stably storing" refers to storage conditions that preserve the items stored in an unchanged or substantially unchanged condition for a period of time longer than the item would be unchanged absent the specific storage conditions. In the context of DNA storage, "stably storing" may refer to storing DNA at room temperature and relative humidity of approximate 50% for greater than 10 years with less than 1% degradation. "Stably storing" may also refer to a technique or structure for storage the reduces degradation of the items stored to a rate that is less than half that of items stored under similar conditions without use of the specific storage technique or structure.

Figure 1:
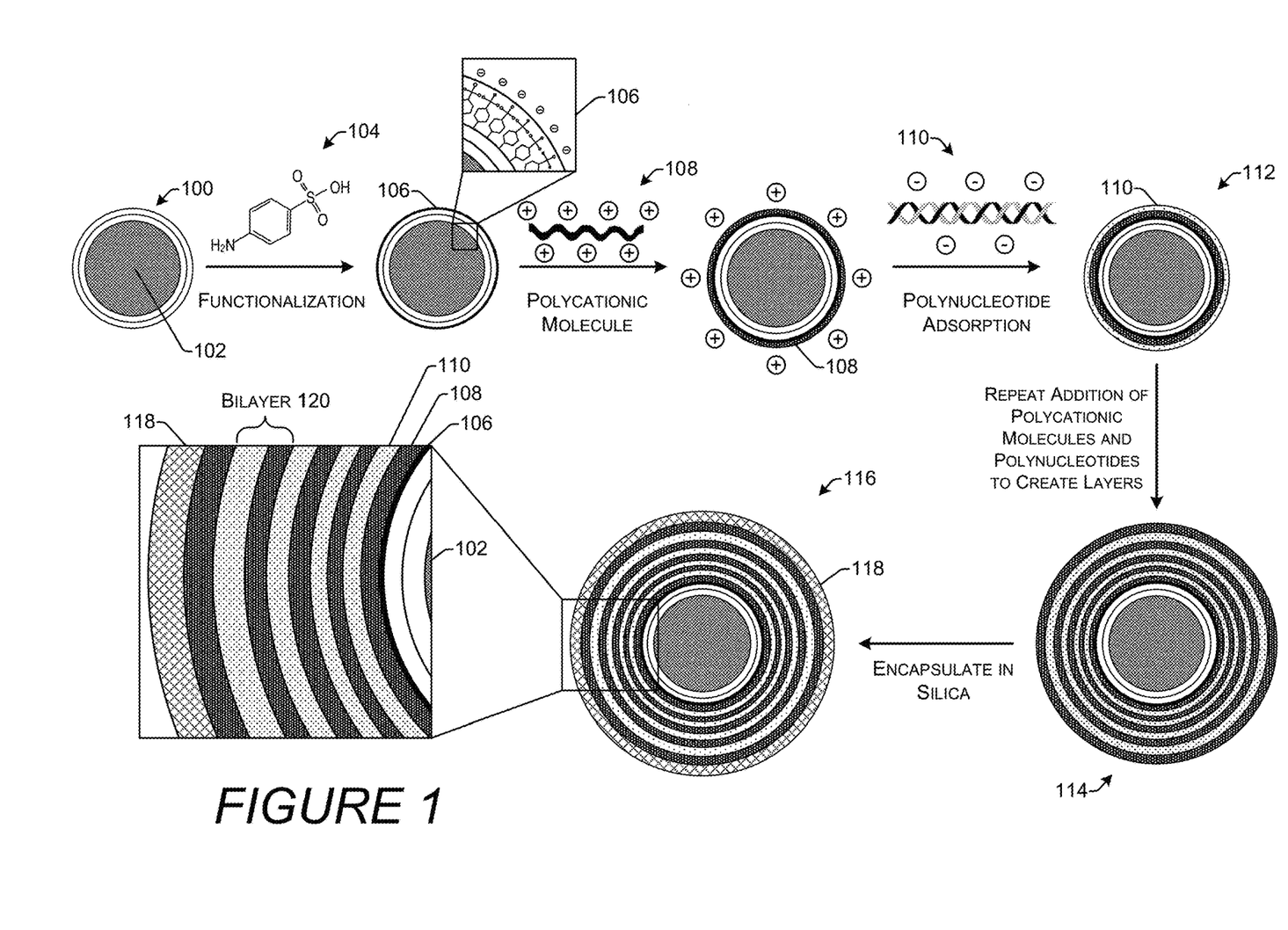
FIG. 1 is a diagram illustrating a structure and process for using a magnetic nanoparticle to stably encapsulate multiple layers of DNA in silica.

FIG. 1 illustrates a schematic representation of a technique for stably storing DNA on a nanoparticle encapsulated in silica and the encapsulate created by this technique. A nanoparticle 100 prior to functionalization or adsorption of products to its surface has a diameter of approximately 100 nm or less. In an implementation, the diameter may be approximately 50 nm. Nanoparticle 100 may have a core 102. The core 102 may be metallic or nonmetallic. Examples of metallic cores include iron, cobalt, nickel, and alloys thereof. Examples of nonmetallic cores include iron oxide, cobalt oxide, nickel oxide, and silica. Techniques for creating nanoparticles out of these materials are known to those of ordinary skill in the art.

In an implementation, the core 102 may be magnetic. The core 102 may have a saturation magnetization of greater than 50, 60, 70, 80, 90, 100, 110, 120, 130, 140, or 150 EMU per gram of nanoparticles 100. In an implementation, the saturation magnetization of the core 102 may be between 80-140 EMU/g given a magnetic field of one Tesla. The material for the core 102 may be selected to achieve a given saturation magnetization.

The nanoparticle 100 may have a carbon coating. The carbon coating may have a mean thickness approximately one nm. Without being bound by theory, it is believed that the carbon coating of is chemically related to the structure of graphite layers or multiwalled carbon nanotubes, and thus is amenable to similar functionalization chemistry. Therefore, a functionalization that may be applied to a graphite layer or carbon nanotube may also be applied to a carbon-coated nanoparticle. TurboBeads are one example of a nanoparticles that have carbon-coated cores. However, other types of nanoparticles are also suitable.

The nanoparticle 100 may be functionalized to create a functionalized surface layer 106. Functionalization may add any type of functional group to the nanoparticle 100 that is capable of attaching to the surface of the core 102 or carbon coating if present. Nanoparticle 100 may be functionalized by the use of a functionalization agent 104 having diazonium chemistry yielding chloro-, nitro-, and amino-functionalized nanoparticles. Nanoparticle 100 may also be functionalized by with ammonium groups using N-trimethoxysilylpropyl-N,N,N-trimethyl-ammonium chloride. FIG. 1 illustrates sulfonate functionalization. A sulfonate is a salt or ester of a sulfonic acid. It contains the functional group R—$SO_3^-$. In an implementation, nanoparticle 100 may have an iron core 102 with a carbon shell and sulfonate functionalization. The functionalization may place a negative charge on the outer surface of the nanoparticle 100.

A polycationic molecule 108 such as a polycationic polymer may be bound to the negatively-charged functional groups through electrostatic forces. The polycationic molecule 108 may be a polycationic linear macromolecule such as polyethyleneimine (PEI), poly-1-lysine (PLL), diethylaminoethyl-dextran (DEAE-dextran), or a branched polymer such as poly(amidoamine) (PAMAM) dendrimers. PEI or polyaziridine is a polymer with repeating unit composed of the amine group and two-carbon aliphatic $CH_2CH_2$ spacer. Linear polyethyleneimines contain all secondary amines. PLL is a specific chiral configuration of the synthetic polymer α-polylysine with L-lysine at lysine's central carbon. DEAE-dextran is a positively charged dextran derivative that binds and interacts with negatively-charged DNA molecules and via an unknown mechanism. PAMAM, is a class of dendrimer which is made of repetitively branched subunits of amide and amine functionality. PAMAMs have a sphere-like shape overall and are typified by an internal molecular architecture including tree-like branching, with each outward 'layer,' or generation, containing exponentially more branching points. Surface amine residues on PAMAM dendrimers bind to the phosphate backbone of DNA through charged interactions.

Addition of the polycationic molecule 108 may performed by vortexing the nanoparticles 100 with the polycationic molecules 108 followed by ultrasonification. This results in the nanoparticle 100 having an outer layer of the polycationic molecule 108 that is positively charged. The positively charged surface is amenable for adsorption of negatively-charged polynucleotides 110 such as DNA.

The nanoparticle 100 may then be contacted with polynucleotides 110 to form a polynucleotide-coated nanoparticle 112. Polynucleotide 110 be present in a solution such as an annealing buffer. As mentioned above, the polynucleotide 110 may be DNA, RNA, single-stranded (ss), double-stranded (ds), hybrids, and/or include unnatural bases. The length of the polynucleotides 110 may be approximately 80-300 base pairs (bp), approximately 100-200 bp, approximately 120-180 bp, or approximately 150 bp. The polynucleotides 110 may encode digital information. Addition of the polynucleotide is 110 may be followed by vortexing and ultrasonification. Although ultrasonification can fragment genomic DNA, polynucleotides several hundreds of bp in length are not damaged by ultrasonification. The polynucleotide-coated nanoparticle 112 has at this point a single layer of polynucleotide 110 on the outermost surface.

Addition of the polycationic molecules in the polynucleotides are repeated to create alternating layers on a layered particle 114. In this illustrative example, there are four polynucleotide 110 layers in the layered particle 114. Without being bound by theory, it is believed that the alternating positive and negative charges of the layers creates a stable structure through electrostatic forces. Repeating these steps multiple times involves repeatedly separating particles from a supernatant. Thus if the core 102 is magnetic, a magnetic separator may be used to facilitate the separation. If the core 102 is not magnetic, other techniques such as filtering and drying may be used to separate the particles from the supernatant.

After multiple layers of polycationic molecules 108 and polynucleotide 110 are added, an "encapsulate" 116 is created by encapsulating the layered particle 114 in silica 118. In an implementation, and to further protect the polynucleotide 110, the final exterior layer before addition of the silica 118 may be the polycationic molecule 108. A single layer of polycationic molecule 108 and the adjacent single layer of polynucleotides 110 may be referred to as a polyanion/polycation bilayer 120 or simply "bilayer." Silica 118 may be added by contacting the layered particle 114 with one or more tetra alkoxysilanes. In an implementation, the tetra alkoxysilane(s) may have an alkoxy chain with between one and five carbon atoms. For example, the tetra alkoxysilane may be tetramethyl orthosilicate, tetraethyl orthosilicate (TEOS), tetrapropyl orthosilicate, tetrabutyl orthosilicate, tetrapentyl orthosilicate, or mixtures thereof.

In an implementation, the tetra alkoxysilane is TEOS. TEOS is a chemical compound with the formula $Si(OC_2H_5)_4$. TEOS is a colorless liquid that degrades in water. TEOS is the ethyl ester of orthosilicic acid, $Si(OH)_4$. It is the most prevalent alkoxide of silicon. TEOS easily converts to silicon dioxide upon the addition of water. This hydrolysis reaction is an example of a sol-gel process. The side product is ethanol. The reaction proceeds via a series of condensation reactions that convert the TEOS molecule into a mineral-like solid via the formation of Si—O—Si linkages. Rates of this conversion are sensitive to the presence of acids and bases, both of which serve as catalysts.

The silica-containing compound may be an aqueous solution and mixed with the layered particles 114 for an extended period of time such as several hours or days. The mixing may be facilitated by use of a shaker. In an implementation, the mixing may be performed for 24 hours, 48 hours, 72 hours, or 96 hours. Longer periods of mixing may result in a thicker silica 118 shell forming around the layered particle 114.

In an implementation, approximately 60% of the encapsulate's 116 weight may be silica 118. Thus, the silica layer 118 may form a very dense shell around the particle. For example, the silica shell may be approximately 5-15 nm thick. Addition of multiple layers including the silica 118 may cause the diameter of the encapsulate 116 to grow to around 200 nm. The silica 118 and other layers around the nanoparticle 100 may reduce the magnetic performance. For example, if, in a one Tesla magnetic field, the nanoparticle 100 has a saturation magnetization of approximately 50 EMU/g then the encapsulate 116 may have a saturation magnetization of approximately 19 EMU/g. The multiple layers of polynucleotides 110 enable the encapsulate 116 to be loaded with more polynucleotides 110 than other configurations that do not use layering. For example, encapsulates 116 may be loaded with polynucleotides 110 such that the structure comprises more than about 1%, 2%, 3%, 4%, 5%, 6%, 7%, 8%, or 9% polynucleotides 110 by weight. In an implementation, the encapsulate 116 may have about 6-8% (wt/wt) polynucleotides 110.

Illustrative Processes

For ease of understanding, the processes discussed in this disclosure are delineated as separate operations represented as independent blocks. However, these separately delineated operations should not be construed as necessarily order dependent in their performance. The order in which the process is described is not intended to be construed as a limitation, and any number of the described process blocks may be combined in any order to implement the process, or an alternate process. Moreover, it is also possible that one or more of the provided operations is modified or omitted.

Figure 2:
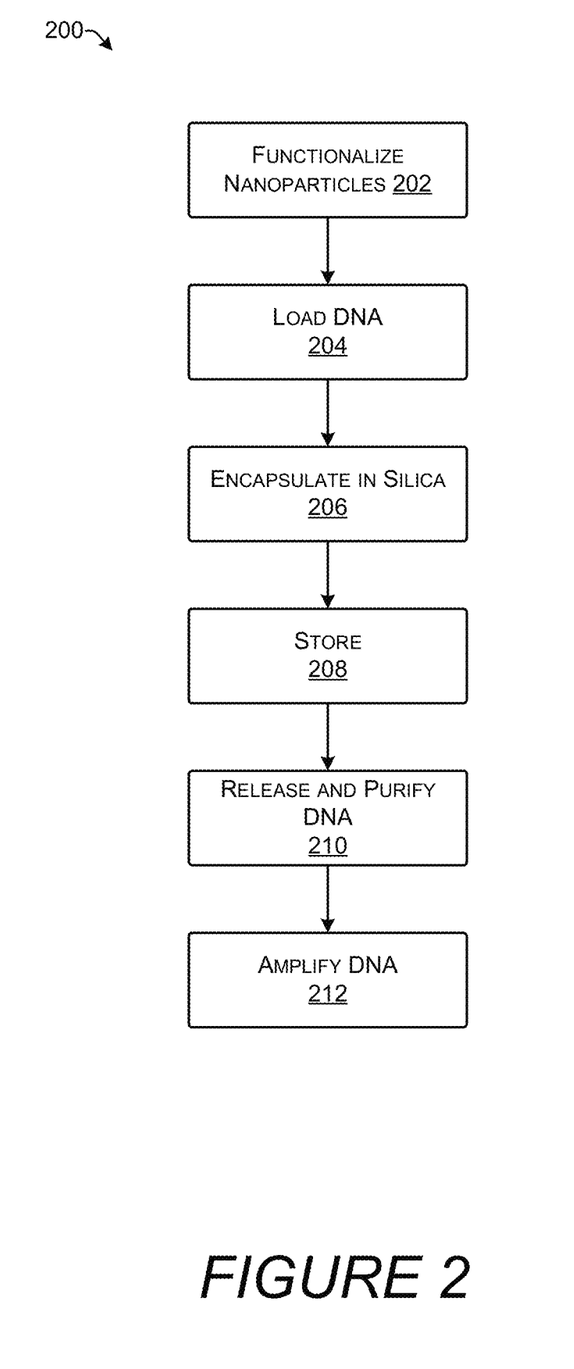
FIG. 2 is a flow diagram showing an illustrative process for encapsulating DNA in silica and recovering the DNA following storage.

FIG. 2 shows process 200 for encapsulating DNA in silica and then recovering the DNA following storage. The DNA may be used for storing digital information and encapsulation in silica may provide stable, long-term storage that protects the DNA from degradation.

At 202, nanoparticles may be functionalized. The nanoparticles may be made of pure metal, metal alloys, metal oxides, or other compounds. In an implementation, the nanoparticles may be magnetic. Functionalization may be achieved by attaching charged functional groups to the surface of the nanoparticles. The functional groups may be positively charged or negatively charged. The functional groups may be sulfonate, ammonium, chloro-, nitro-, or amino-groups. Functionalization may be achieved by known chemical processes based on the composition of nanoparticle and the functional group to be added. Functionalization may be performed by mixing the nanoparticles with a strong acid (e.g., HCl) in an aqueous solution in an ultrasonic bath (Elmasonic "P" series) at 25° C. for 30 minutes. The result of functionalization may be a (magnetic) nanoparticle that has a negatively-charged surface. Alternatively, process 200 may begin with commercially available nanoparticles that are already functionalized. For example, the nanoparticles may be sulfonate functionalized TurboBeads (50 mg/ml).

At 204, DNA is loaded onto the nanoparticles. The DNA may be in a solution of annealing buffer (e.g., at a concentration of 50 μg/ml). The annealing buffer may be any standard buffering solution for DNA such as 400 mM Tris-HCl, 500 mM NaCl, and 100 mM $MgCl_2$. The DNA molecules in the solution may have a length of about 100-300 bp. In an implementation the length of the DNA molecules may be approximately 150 bp.

If the functional groups on the nanoparticles are positively charged, DNA may be adsorbed to the surface of the nanoparticle by electrostatic forces. If the functional groups are negatively charged, DNA may be loaded onto negatively-charged nanoparticles by first contacting the nanoparticles with positively charged molecules. A polycationic molecule such as PEI may be used. The polycationic molecule may be diluted in ultrapure water (e.g. to a concentration of 2.6 mg/mL). As used herein, "ultrapure water" refers to water having a purity such that resistivity is 18.2 MΩ·cm at 25° C. or "type 1" water as specified in ISO (International Organization for Standards) 3696. One source of ultrapure water is Milli-Q™ water available from Millipore Corporation.

The nanoparticles may be suspended by briefly vortexing in ultrapure water followed by ultrasonification in an ultrasonic bath. In an implementation, 2 μL of nanoparticles may be mixed with 50 μL of ultrapure water in a 2 mL microcentrifuge tube and placed in the ultrasonic bath for one minute. A magnetic separator (OceanNanoTech, SuperMag Multitube Separator) may be used to separate magnetic nanoparticles from the supernatant after the ultrasonic bath. The PEI solution (300 μL), or another cationic polymer, may be added to the microcentrifuge tube, vortexed and then ultrasonicated for approximately 30 seconds. A block magnet, for example a neodymium magnet, may be used to pull the nanoparticles to one side of the microcentrifuge tube while discarding the supernatant. The nanoparticles may then be washed by addition of 200 μL of ultrapure water, brief vortexing, and ultrasonification for 10 seconds. Following this wash, 200 μL of the DNA solution may be added to the microcentrifuge tube, vortexed, and place in the ultrasonic bath for 30 seconds. During this time the some or all of the DNA molecules have been adsorbed onto the polycationic molecules. The supernatant, which potentially contains DNA, may be collected and reused.

The nanoparticles may again be washed by addition of 100 μL of ultrapure water, a brief vortex, and ultrasonification for 10 seconds. The block magnet may be used to separate the particles from the solution and the supernatant discarded. Contacting the nanoparticles with PEI followed by DNA according to the procedures set forth above may be repeated multiple times to create multiple bilayers on the nanoparticle. Creating multiple layers of DNA on the nanoparticle provides a greater density of DNA (i.e., more DNA per nanoparticle) then just coating the nanoparticle with a single layer. A final step of the DNA loading may be contacting the nanoparticles with the PEI solution so that the last layer is the polycationic molecule.

At 206, the nanoparticles covered with multiple layers of polycationic molecules and DNA may be encapsulated in silica. The block magnet is used to separate the nanoparticles from any remaining supernatant. In an implementation, 1000 µL of ultrapure water is added to the nanoparticles in the microcentrifuge tube and placed in the ultrasonic bath for 30 seconds. This is followed by addition of a tetra alkoxysilane such as TEOS. For example, 5 µL of TEOS may be added to the microcentrifuge tube while in the ultrasonic bath. The microcentrifuge tubes containing the nanoparticles, the ultrapure water, and the TEOS may be placed in a shaker at approximately 500-2000 revolutions per minute (RPM). Shaking may be maintained for a prolonged period of time such as one day, two days, three days, four days, five days, or longer.

At 208, the silica-coated nanoparticles or "encapsulates," may be stored. The encapsulates may be separated from supernatant by applying a magnetic field gradient such as by use of the block magnet. The encapsulates may be stored in the microcentrifuge tubes or transferred to another vessel for storage. Storage conditions may be selected to further enhance longevity of the samples. For example, the DNA in the encapsulates may be stored at cool temperatures with low humidity such as, for example, 9° C. and 20% relative humidity. When encased in silica and stored under favorable conditions, the DNA may be preserved without significant degradation for hundreds, thousands, or potentially millions of years. For example, encapsulation in silica may achieve levels of dsDNA stability such that there is <0.2, <0.3, <0.5, <1.0, or <2.0 ACq per day when stored at 70° C. and 50% relative humidity (RT). ACq is a measurement in the change in the number of cycles of quantitative PCR required to increase the amount of DNA in the sample above a detection threshold, and for sequences with an optimal PCR efficiency (100%), a ACq of 1 is equivalent to a detection loss of 50% of the initially present DNA. A larger value for Cq indicates a smaller starting amount of DNA requiring a greater number of PCR amplification cycles.

The storage in silica may also make the DNA more resistant to chemical attack such as by DNA degrading agents. Reactive oxygen species (ROS) are one type of DNA degrading agent. ROS are chemically reactive chemical species containing oxygen. Examples include peroxides, superoxide, hydroxyl radical, and singlet oxygen. A high percentage of the DNA encapsulated in silica can survive exposure to ROS—e.g., more than 30%, 40%, 50%, 60%, 70%, 80%, or 90%. Thus, if a layer of silica can be formed over the DNA such as by the techniques discussed herein using nanoparticles or other substrates, the structure will help to at least partially prevent DNA degradation by strong chemicals. The results of an ROS test showing improved DNA stability are evidence that the techniques are silica encapsulation form a non-porous glass layer around the DNA. If the silica layer is not fully formed or if it is porous, greater levels of DNA degradation are to be expected.

At 210, the DNA is released from silica encapsulation and purified. At some point, the DNA may be accessed for sequencing by an oligonucleotide sequencer or for other processing. Because the silica encapsulation protects the DNA from degradation it also prevents most molecular biology techniques from acting on the DNA. Thus, the DNA may need to be removed from the silica shell in order to be sequenced or otherwise used. Purification removes remnants of the silica, salts, and other compounds from the solution leaving "clean" DNA that is ready for further processing.

Silica dissolves rapidly in fluoride-containing solutions (forming $SiF_6^{2-}$). Thus, an etching buffer containing fluoride may be used to dissolve the silica. The compatibility of dilute etching solutions and DNA (DNA is not affected by $F^-$ ions) has previously been shown. The etching buffer may be a mixture of buffering agent such as ammonium fluoride ($NH_4F$) and hydrofluoric acid (HF). In an implementation, the etching buffer may be prepared by dissolving 0.23 g of ammonium hydrogen difluoride ($NH_4FHF$, puriss, Sigma-Aldrich, cat. no. 30101) in 5 mL of $H_2O$ and 0.19 g of $NH_4F$ (puriss, Sigma-Aldrich, cat. no. 30101) in 5 mL of $H_2O$ then mixing the two solutions together. The pH is approximately 4 and should be measured with pH paper not a pH electrode. The vapors of buffered hydrogen fluoride solutions can penetrate skin and rapidly damage cells and bones. Excess etching buffer may be disposed of in a plastic container of calcium carbonate.

The silica may be removed by using heated purification columns. The heat may be provided, for example, by the thermomixer set to 95° C. One type of purification column that may be used are those provided in the QIAquick PCR purification kit (Qiagen, cat. no. 28104).

Nanoparticles may be processed prior to loading onto the purification columns. In an implementation, the nanoparticles may be immersed in 20 µL of ultrapure water and 10 µL of etching buffer for approximately five minutes. This is followed by neutralizing the pH through adding 10 µL of potassium phosphate buffer (0.5 M, pH 7), vortexing, and adding 100 µL of a release solution. The release solution may be made by diluting 40 mg of poly(acrylic acid) sodium (PAS) in 50 mL of ultrapure water to a concentration of 0.8 mg/mL and mixing that with sodium chloride diluted in ultrapure water until saturation at room temperature in a ratio of PAS:NaCl=20:80. PAS is a polyanionic molecule that displaces the DNA from the PEI. Addition of the release solution may be followed by vortexing and ultrasonification for 30 seconds. The microcentrifuge tube containing the nanoparticles can be placed into the preheated thermomixer and shaken for two minutes at 900 RPM.

After shaking, 650 µL of buffer PB (Qiagen, cat. no. 28104) may be added to the microcentrifuge tube and the contents transferred to the purification column. Buffer PB is used in DNA cleanup procedures and enables efficient binding of single- or double-stranded polynucleotides to a membrane of the purification column. Buffer PB contains a high concentration of guanidine hydrochloride and isopropanol.

The purification column may be placed on a centrifuge (Eppendorf Centrifuge 5424 R) and spun for one minute at 17,900 cfg. Discard flow through and add 700 µL of a wash buffer such as buffer PE (Qiagen, cat. no. 19065). Centrifuge for one minute at 17,900 cfg and discard flow-through. The washing with buffer PE may be repeated.

The purification column is then placed into a microcentrifuge tube and 200 µL of preheated etching buffer is added to the microcentrifuge tube. The microcentrifuge tube containing the purification column is shaken for two minutes at 900 RPM. Next the microcentrifuge tube is centrifuged for one minute at 17,900 cfg. This produces purified DNA free from the silica shell. Although the illustrative purification procedure described above uses a specific commercial kit, any technique for purifying DNA that is compatible with buffered hydrogen fluoride solutions may be used.

At 212, the DNA is amplified. The DNA may be amplified by polymerase chain reaction (PCR) which increases the amount of DNA available for sequencing or other processing.

Figure 3:
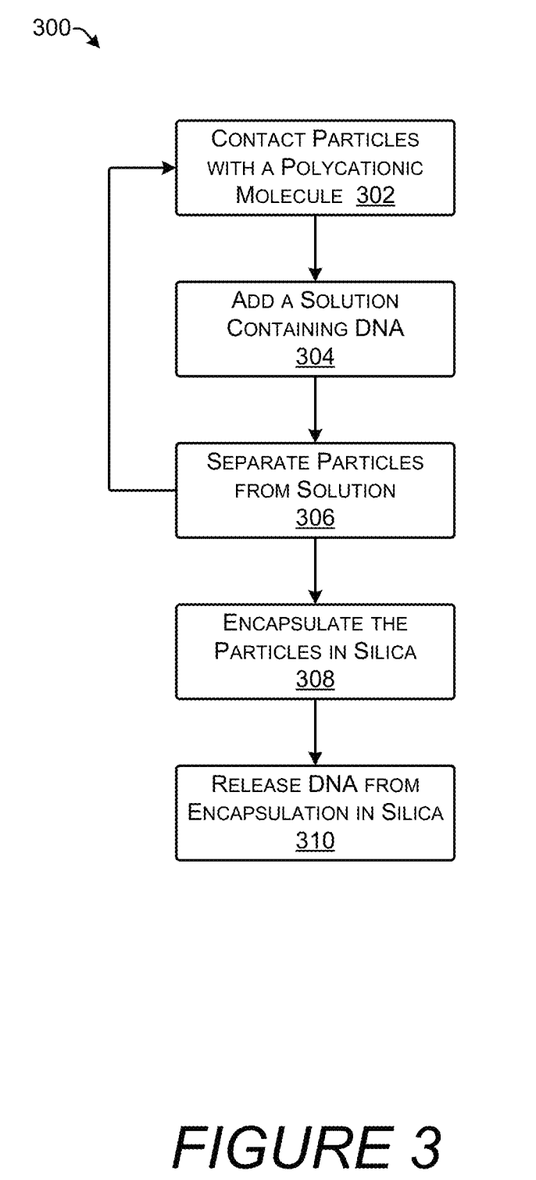
FIG. 3 is a flow diagram showing an illustrative process for encapsulating particles containing multiple layers of DNA in silica.

FIG. 3 shows process 300 for encapsulating particles containing multiple layers of DNA in silica.

At 302, particles having magnetic cores are contacted with a polycationic molecule. In an implementation, the polycationic molecule may be a polycationic polymer such as PEI. The polycationic molecule may be polyethyleneimine (PEI), poly-1-lysine (PLL), diethylaminoethyl-dextran (DEAE-dextran), poly(amidoamine) (PAMAM) dendrimers, or a mixture thereof.

The magnetic particles may be nanoparticles and in one implementation they may be carbon-coated metal nanoparticles. The magnetic cores of the nanoparticles may be formed from a metal such as iron, cobalt, nickel, and alloys thereof. The magnetic cores may also be formed from metal oxides. The saturation magnetization of the magnetic cores may be greater than 50 EMU/g, greater than 80 EMU/g, or greater than 100 EMU/g.

Contacting of the polycationic molecule with the particles may be performed by vortexing the particles in a solution containing the polycationic molecule. The contacting may further include use of ultrasound to agitate the particles in the presence of the polycationic molecule solution.

At 304, a solution of polynucleotides such as dsDNA may be added to the magnetic particles. The polynucleotides may have lengths of approximately 80-300 bp, approximately 100-200 bp, approximately 120-180 bp, or approximately 150 bp. The polynucleotides may encode digital information such as all or a portion of a computer file. The polynucleotides may be provided in an aqueous solution such as an annealing buffer at a concentration of, for example, around 20, 30, 40, 50, 60, 70, 80, 90, or 100 µg/mL.

At 306, the magnetic particles are separated from the solution. Separating the magnetic particles from the solution may be performed by applying a magnetic field gradient. The magnetic field gradient may be created by a permanent magnet such as commercial neodymium magnet (e.g., magnetic induction of 1.4 Tesla). However, other sources of a magnetic field gradient such electromagnets are equally suitable. The magnet may be a block magnet or part of a device such as a magnetic separator. Alternatively, the particles may be separated from the solution by physical separation such as filtering and/or drying.

After separation from the solution, the magnetic particles may be repeatedly contacted with the polycationic molecule and DNA. Thus, steps 302, 304, and 306 may repeated at least two times, at least three times, at least four times, or more. Each iteration through these steps adds an additional polyanion/polycation bilayer comprising the DNA and polycationic molecule. Adding additional layers of DNA onto the magnetic particles may increase DNA density.

At 308, the particles are encapsulated in silica. Encapsulating the particles in silica creates silica-encapsulated particles which may also be referred to as "encapsulates." The particles may be encapsulated in silica by contacting the particles with a tetra alkoxysilane. The tetra alkoxysilane may be tetramethyl orthosilicate, tetraethyl orthosilicate (TEOS), tetrapropyl orthosilicate, tetrabutyl orthosilicate, tetrapentyl orthosilicate, or mixtures thereof. Contacting the particles with the tetra alkoxysilane may be performed for a prolonged period of time such as 3 hours, 12 hours, 24 hours, 48 hours, 72 hours, 96 hours, or more. Longer periods of mixing may result in a thicker silica shell forming around the magnetic particle. The particles may be contacted with the tetra alkoxysilane while in an ultrasonic bath and the mixture of particles and tetra alkoxysilane may be shaken continuously or intermittently during the period of time when the silica shell is forming.

At 310, the polynucleotides may be released from the silica-encapsulated particles by contacting the particles with an etching buffer and a polyanionic molecule such as PAS. Releasing DNA from a silica encapsulation may be performed after a period of storing the DNA. The period may be multiple days, weeks, months, years, centuries, or longer. A buffered hydrogen fluoride solution may be used to dissolve the silica. One suitable fluoride-containing solution is $NH_4FHF/NH_4F$.

EXAMPLES

In the following examples the nanoparticles were carbon-coated TurboBeads with iron cores and sulfonate surface functionalization. The polynucleotides adsorbed to the nanoparticles were 150 bp strands of dsDNA. PEI (branched, Mw 1200, Polysciences, cat. no. 06088) was used as the polycationic molecule.

Figure 4:
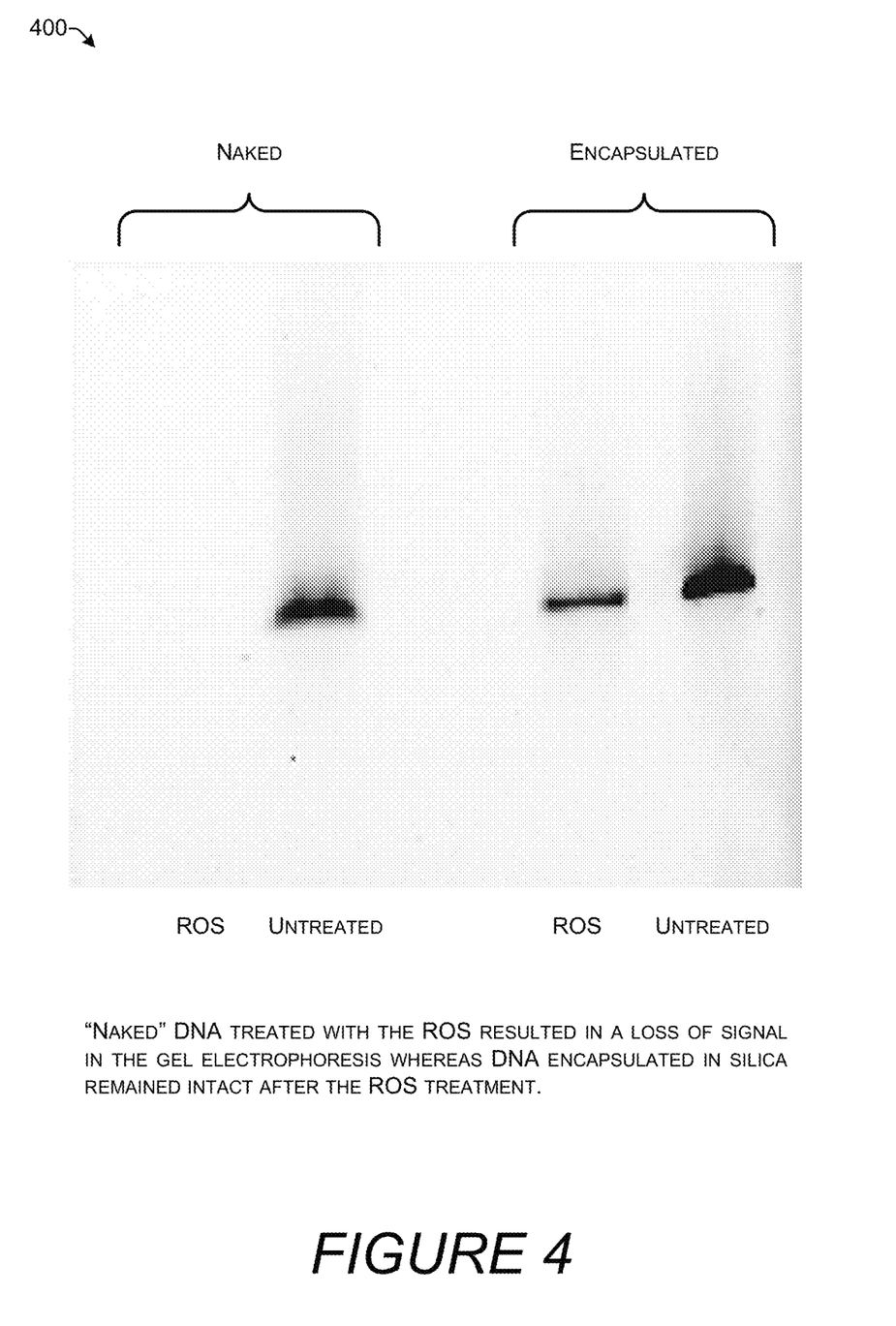
FIG. 4 is an image of electrophoretic gel showing that encapsulation in silica protects DNA from degradation by reactive oxygen species (ROS).

FIG. 4 is an image 400 of electrophoretic gel showing that encapsulation in silica protects DNA from degradation by DNA degrading agents such as reactive oxygen species (ROS). Four layers of DNA were adsorbed on the surface of the nanoparticles. The ROS test was performed by adding a solution of L-Ascorbic acid (20 mM), $H_2O_2$ (20 mM), and $CuCl_2$ (500 µM) for 10 minutes to the naked DNA and encapsulated nanoparticles. The reaction was quenched by addition of ethylenediaminetetraacetic acid (EDTA). Concentration of the DNA was measured using the Qubit™ ssDNA Assay Kit (ThermoFisher Scientific cat. no. Q102212) and a Qubit fluorometer. Remaining DNA percentage was compared to a control sample including the quenched reactive solution.

"Naked" DNA when exposed to ROS resulted in a complete loss of signal in the gel. A strong signal was present in the gel for the control that was not exposed to ROS. DNA quantification by the Qubit assay identified that 14.29% of the starting amount of naked DNA remained after exposure to ROS. Thus, absent a protective layer exposure to ROS is effective at degrading DNA.

Encapsulated DNA was much more resistant to degradation by ROS. The gel shows a strong band for DNA encapsulated in silica following exposure to ROS. However, there is a decrease in the band strength compared to the encapsulated DNA control. ROS exposure reduced the amount of DNA encapsulated in silica to 52.34% of the starting amount. Thus, silica encapsulation resulted in over three times more DNA remaining after ROS treatment.

Figure 5:
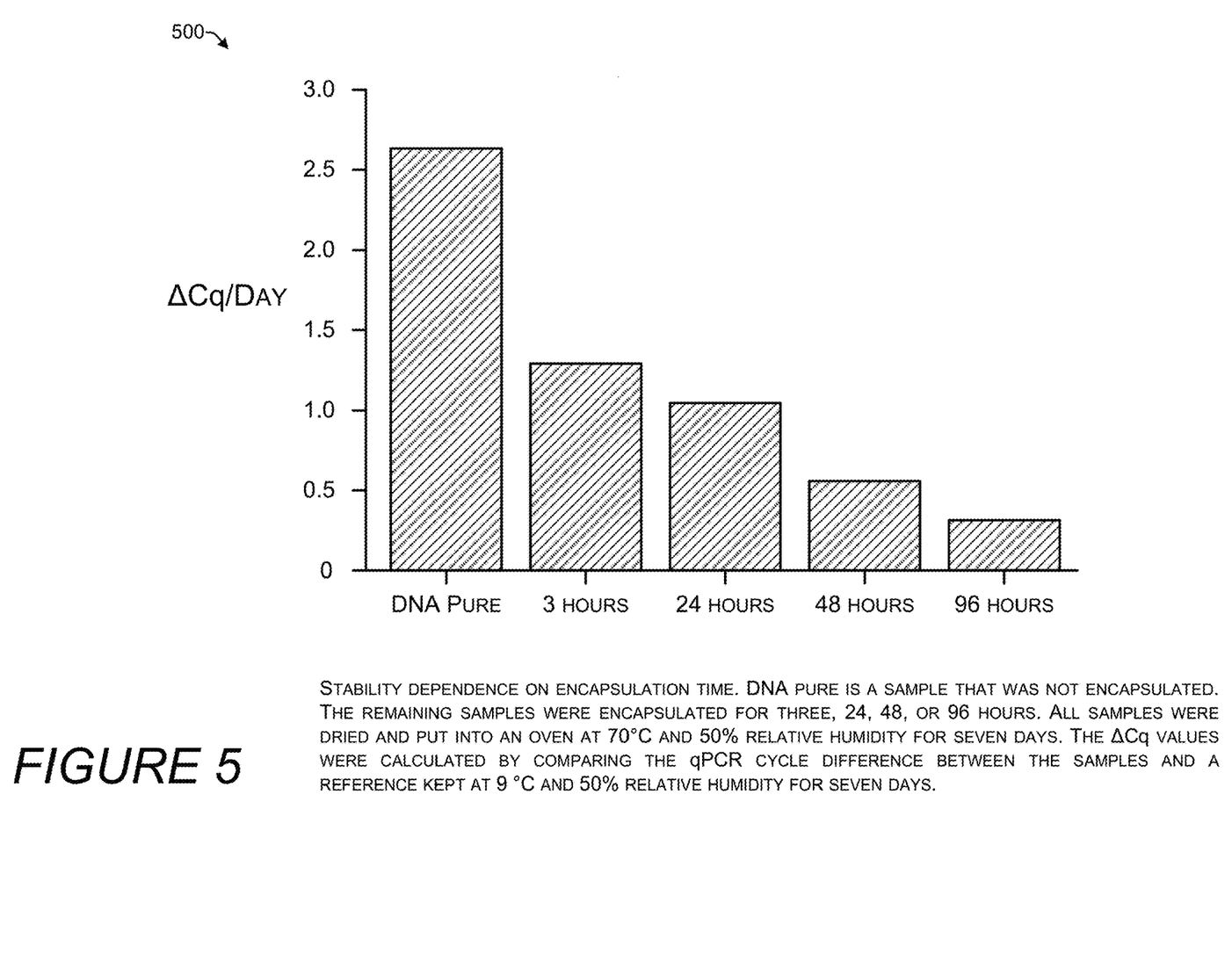
FIG. 5 is a bar chart showing the effects of the increased silica encapsulation on stability of the DNA. As the more time is provided for the silica encapsulation process, stability increases. Higher bars indicate a high rate of degradation and lower bars indicate greater stability.

FIG. 5 is a bar chart 500 showing the effects of increased silica encapsulation on stability of DNA. Silica coating forms within hours but additional time allows the formation of a more protective coating. Samples were placed in 70° C. and 50% RH for seven days to simulate the amount of thermal stress the DNA would experience stored at 9° C. for 2000 years. References samples prepared identically were stored at 9° C. and 50% RH for the same seven days. All samples started with identical quantities of DNA.

The samples were exposed to TEOS (>99.0%, Aldrich, cat. no. 86578) with shaking in a shaker (ThermoMixer Temperature Control Device) at 1100 RPM for the length of time indicated in the x-axis. "DNA Pure" represents "naked" DNA that is not encapsulated in silica or otherwise protected.

The height of the bars is calculated by comparing the quantitative PCR (qPCR) cycle difference between the samples stored at 70° C. and the reference samples after seven days and dividing by seven to arrive at a per-day change. qPCR uses the linearity of DNA amplification to determine absolute or relative quantities of DNA in a sample. By using a fluorescent reporter in the reaction, it is possible to measure DNA generation in the qPCR assay as the PCR reaction proceeds in real time. The number of PCR cycles at which the fluorescence exceeds a detection threshold and becomes measurable is called the quantification cycle (Cq). Starting samples that include a larger amount of DNA reach this threshold with fewer PCR cycles than samples with a smaller amount of DNA. Thus, Cq values are inversely proportional to the amount of target DNA in the sample. The difference in the Cq value of the sample stored at 70° C. and Cq value of the reference sample stored at 9° C. (ΔCq) indicates how much more the sample stored at a high temperature degraded. If the difference was zero, that would indicate that the elevated temperature did not increase the amount of DNA degradation.

As evidenced by the decrease in the height of the bars as the encapsulation time increased, the more time that is provided for the silica encapsulation process, the more stability increases. A single cycle of PCR results in a doubling of the amount of DNA, so decrease of one in a Cq value indicated a doubling the starting DNA amount. The DNA Pure sample, without silica protection, degraded the most with a ΔCq per day value of over 2.64 indicating that each day during storage at 70° C. the amount of DNA decreased by over 2.5 times. The results shown in bar chart 500 are reproduced in tabular form in Table 1 below.

| Encapsulation Time (hours) | ΔCq/day |
|---|---|
| None (DNA Pure) | 2.64 |
| 3 | 1.293 |
| 24 | 1.055 |
| 48 | 0.5628 |
| 96 | 0.314 |

Thus, if silica encapsulation is allowed to continue for one day (24 hours), the encapsulated DNA decreases by about half each day in storage at 70° C. However, if the encapsulation time is extended to four days (96 hours) the ΔCq per day is about 0.3 which corresponds to slightly less than a quarter of the original DNA remaining after seven days. Thus, dsDNA stability of <0.4 ΔCq per day is achieved when the DNA-coated microbeads are shaken with TEOS for four days.

Figure 6:
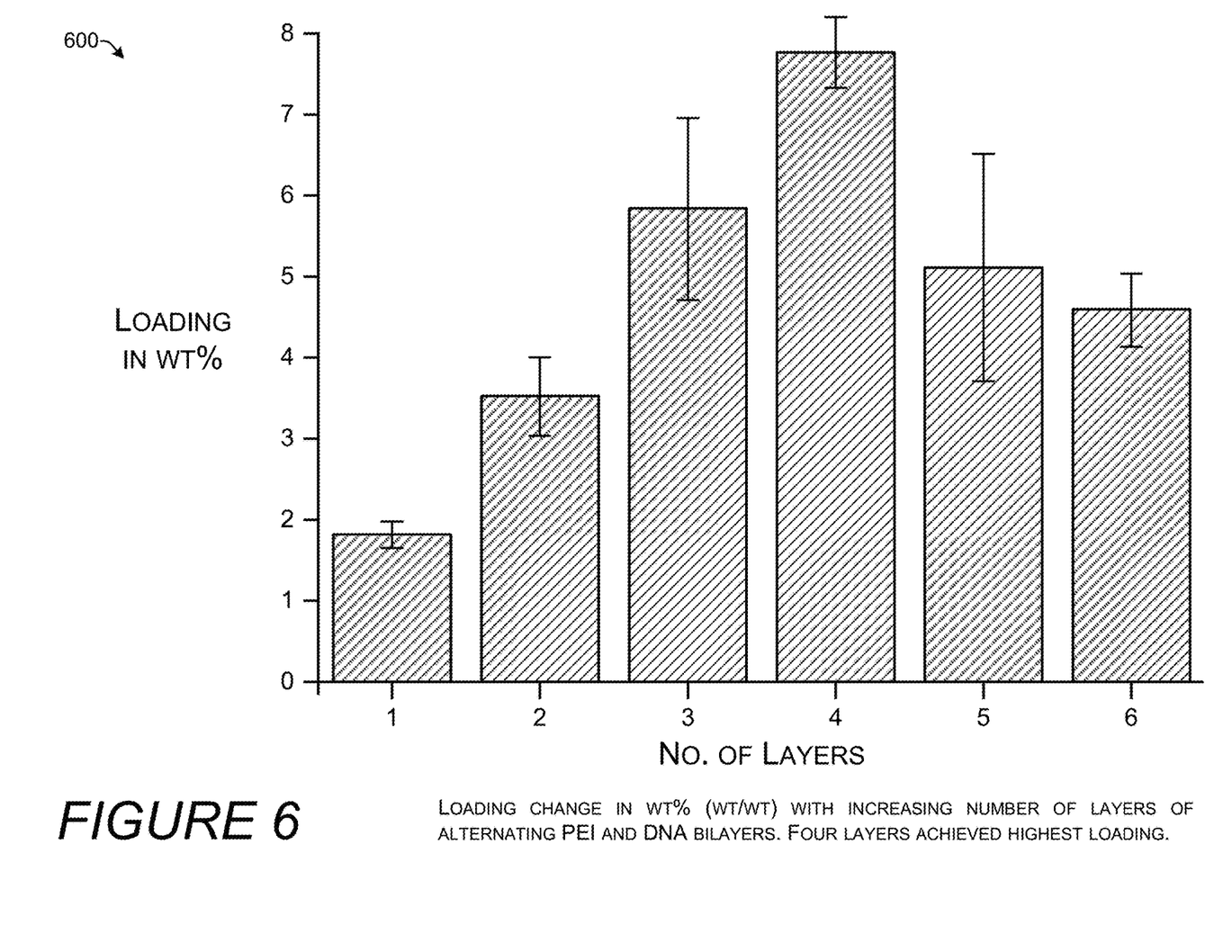
FIG. 6 is a bar chart showing how the storage density measured in weight percent of DNA varies with the number of layers of DNA. Storage density increases up to a total of four layers then decreases again.

FIG. 6 is a bar chart 600 showing how the storage density measured in weight percent (wt %) of DNA varies with the number of layers of DNA. The TurboBeads nanoparticles were prepared as described above and the steps of adding additional layers of polycationic polymer (PEI) and were DNA repeated a variable number of times. Adding an additional layer may correspond to repeating steps 302, 304, and 306 from FIG. 3.

Interestingly, storage density increases up to a total of four layers then decreases. Without being bound by theory, a reason for the decrease in DNA loading after the fourth layer may be adhesion to the walls of the centrifuge tube. The loading density is measured in wt % representing the percent of the total weight of the particles that is DNA. With one layer, only about 2% (wt/wt) is DNA, that increases with four layers to over 7% (wt/wt) but is less than 5% (wt/wt) DNA with six layers.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A multilayered structure for stably storing DNA comprising: a negatively-charged magnetic core; a plurality of alternating layers of DNA and of a polycationic molecule; and silica coating, wherein the multilayered structure contains at least 1% DNA by weight and protects the DNA such that at least 50% of the DNA survives exposure to a DNA-degrading agent.

Clause 2. The multilayered structure of clause 1, wherein the negatively-charged magnetic core comprises metallic Fe, Co, or Ni; a metallic alloy of Fe, Co, or Ni; or a composition thereof.

Clause 3. The multilayered structure of any of clauses 1-2, wherein the negatively-charged magnetic core has a functionalized surface layer imparting a negative charge.

Clause 4. The multilayered structure of any of clauses 1-3, wherein the negatively-charged magnetic core has a saturation magnetization of at least 50 EMU/g prior to adsorption of the DNA or of the polycationic molecule.

Clause 5. The multilayered structure of any of clauses 1-4, wherein the plurality of alternating layers consists of four layers.

Clause 6. The multilayered structure of any of clauses 1-5, wherein the silica coating is formed from one or more tetra alkoxysilanes.

Clause 7. The multilayered structure of any of clauses 1-6, wherein the polycationic molecule comprises polyethyleneimine (PEI) poly-1-lysine (PLL), diethylaminoethyl-dextran (DEAE-dextran), or poly(amidoamine) (PAMAM).

Clause 8. The multilayered structure of any of clauses 1-7, wherein the multilayered structure contains at least 7% DNA by weight.

Clause 9. The multilayered structure of any of clauses 1-8, wherein the DNA degrading agent produces reactive oxygen species (ROS).

Clause 10. A method for stably storing polynucleotides comprising:
  a. contacting particles having magnetic cores with a polycationic molecule;
  b. adding a solution of polynucleotides;
  c. separating the particles from the solution;
  d. repeating steps a-c at least once; and
  e. encapsulating the particles in silica to create silica-encapsulated particles.

Clause 11. The method of clause 10, wherein the particles having magnetic cores comprise carbon-coated metal nanoparticles.

Clause 12. The method of any of clauses 10-11, wherein the polycationic molecule comprises polyethyleneimine (PEI).

Clause 13. The method of any of clauses 10-12, wherein the separating the particles from the solution is performed at least in part by applying a magnetic field gradient.

Clause 14. The method of any of clauses 10-13, wherein encapsulating the particles in silica comprises contacting the particles with one or more tetra alkoxysilanes.

Clause 15. The method of clause 14, wherein the contacting the particles with the tetra alkoxysilanes is performed for at least 48 hours.

Clause 16. The method of any of clauses 10-15, further comprising repeating steps a-c at least three times.

Clause 17. The method of any of clauses 10-16, further comprising release of the polynucleotides by contacting the silica-encapsulated particles with an etching buffer and a polyanionic molecule.

Clause 18. An article of manufacture comprising a plurality of polyanion/polycation bilayers encapsulated in silica, wherein the polyanion comprises polynucleotides and the polycation comprises a polycationic molecule.

Clause 19. The article of manufacture of clause 18, wherein the plurality of polyanion/polycation bilayers is overlaid on a negatively-charged magnetic substrate.

Clause 20. The article of manufacture of any of clauses 18-19, wherein polynucleotide content is at least 1% by weight.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention (especially in the context of the following claims) are to be construed to cover both the singular and the plural, unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications (collectively "references") throughout this specification. Each of the cited references is individually incorporated herein by reference for its particular cited teachings as well as for all that they disclose.

The invention claimed is:

1. A method for protecting polynucleotides from degrading agents comprising:
   a. contacting particles having magnetic cores with a polycationic molecule to create polycation coated particles;
   b. adding the polycation coated particles to a solution of polynucleotides to create polynucleotide/polycation coated particles;
   c. separating the polynucleotide/polycation coated particles from the solution;
   d. repeating steps a-c at least once;
   e. encapsulating the polynucleotide/polycation coated particles in silica to create silica-encapsulated particles thereby creating a silica shell over the polynucleotides having a thickness and composition such that at least 50% of the polynucleotides in the silica-encapsulated particles survives exposure to reactive oxygen species for 10 minutes; and
   f. releasing of the polynucleotides by contacting the silica-encapsulated particles with an etching buffer and a polyanionic molecule.

2. The method of claim 1, wherein the particles having magnetic cores comprise carbon-coated metal nanoparticles.

3. The method of claim 1, wherein the polycationic molecule comprises polyethyleneimine (PEI).

4. The method of claim 1, wherein the separating the polynucleotide/polycation coated particles from the solution is performed at least in part by applying a magnetic field gradient.

5. The method of claim 4, wherein the magnetic field gradient is created by a neodymium magnet.

6. The method of claim 1, wherein encapsulating the polynucleotide/polycation coated particles in silica comprises contacting the polynucleotide/polycation coated particles with one or more tetra alkoxysilanes.

7. The method of claim 6, wherein the contacting the polynucleotide/polycation coated particles with the tetra alkoxysilanes is performed for at least 48 hours.

8. The method of claim 6, wherein the one or more tetra alkoxysilanes comprises tetraethyl orthosilicate (TEOS).

9. The method of claim 1, further comprising repeating steps a-c at least three times.

10. The method of claim 1, wherein the polycationic molecule comprises polyethyleneimine (PEI), poly-1-lysine (PLL), diethylaminoethyl-dextran (DEAE-dextran), or poly(amidoamine) (PAMAM).

11. The method of claim 1, further comprising functionalizing the magnetic cores with molecules that impart negative charge.

12. The method of claim 1, wherein adding the polycation coated particles to the solution of polynucleotides comprises adding the polycation coated particles to DNA in an annealing buffer.

13. The method of claim 1, wherein the polyanionic molecule comprises poly(acrylic acid) sodium (PAS).

14. The method of claim 1, wherein at least 90% of the polynucleotides survives exposure to the polynucleotide-degrading agent.

15. The method of claim 1, wherein the silica shell is approximately 5-15 nm thick.

16. The method of claim 1, further comprising collecting the solution generated at c, after separating the polynucleotide/polycation coated particles and reusing the solution during a subsequent step b.

* * * * *